US009623258B2

(12) United States Patent
Trayanova et al.

(10) Patent No.: US 9,623,258 B2
(45) Date of Patent: Apr. 18, 2017

(54) METHOD FOR LOW VOLTAGE DEFIBRILLATION WITH FAR-FIELD STIMULI OF VARIABLE TIMINGS BASED ON FEEDBACK FROM THE HEART

(71) Applicant: THE JOHNS HOPKINS UNIVERSITY, Baltimore, MD (US)

(72) Inventors: Natalia Trayanova, Baltimore, MD (US); Lukas Rantner, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 71 days.

(21) Appl. No.: 14/398,803

(22) PCT Filed: May 6, 2013

(86) PCT No.: PCT/US2013/039680
§ 371 (c)(1),
(2) Date: Nov. 4, 2014

(87) PCT Pub. No.: WO2013/166485
PCT Pub. Date: Nov. 7, 2013

(65) Prior Publication Data
US 2015/0119948 A1    Apr. 30, 2015

Related U.S. Application Data

(60) Provisional application No. 61/642,822, filed on May 4, 2012.

(51) Int. Cl.
*A61N 1/36*   (2006.01)
*A61N 1/39*   (2006.01)
(Continued)

(52) U.S. Cl.
CPC .......... *A61N 1/3906* (2013.01); *A61N 1/395* (2013.01); *A61N 1/3956* (2013.01);
(Continued)

(58) Field of Classification Search
CPC .. A61N 1/3906; A61N 1/3627; A61B 5/0402; A61B 5/0464; A61B 5/7239
See application file for complete search history.

(56) References Cited

U.S. PATENT DOCUMENTS 5,718,718 A    2/1998 Kroll et al.
6,256,535 B1 *  7/2001 Province .............. A61N 1/3956
607/5

(Continued)

OTHER PUBLICATIONS

Fenton, F., et al., "Termination of atrial fibrillation using pulsed low-energy far-field stimulation", Circulation, Aug. 11, 2009, vol. 120, No. 6, pp. 467-476.
(Continued)

*Primary Examiner* — Edward Moran
*Assistant Examiner* — Natasha Patel
(74) *Attorney, Agent, or Firm* — John Hopkins Technology Ventures

(57) ABSTRACT

The present invention includes a method for cardiac defibrillation, especially low-voltage defibrillation, in a subject, including converting fibrillation into tachycardia and using feedback or an estimation thereof from the heart to time stimuli to occur when large amounts of tissue are excitable in the heart of the subject. The resultant tachycardia can then be terminated using a tachycardia termination protocol known to or conceivable by one of skill in the art. The method can be implemented using a currently available defibrillator or an internal cardioverter-defibrillator (ICD) configured to apply a lower voltage shock, such as a far-field stimulation. A device designed especially for the method or another device employing this method can also be used.

(Continued)

Because the proposed defibrillation method requires less energy than current approaches using single biphasic stimulus, defibrillator battery life is improvable or battery size decreasable. The method reduces pain and cellular damage resultant from traditional defibrillation.

27 Claims, 6 Drawing Sheets

(51) Int. Cl.
- *A61B 5/046* (2006.01)
- *A61B 5/0464* (2006.01)
- *A61N 1/362* (2006.01)

(52) U.S. Cl.
CPC ............ *A61N 1/3987* (2013.01); *A61B 5/046* (2013.01); *A61B 5/0464* (2013.01); *A61N 1/3621* (2013.01); *A61N 1/3962* (2013.01)

(56) References Cited

U.S. PATENT DOCUMENTS

| | | |
|---|---|---|
| 2003/0233129 A1* | 12/2003 | Matos .................. A61B 5/0006 607/5 |
| 2006/0161206 A1 | 7/2006 | Efimov et al. |
| 2008/0177341 A1 | 7/2008 | Bowers |
| 2012/0209343 A1* | 8/2012 | Efimov .................. A61N 1/395 607/5 |
| 2013/0296959 A1* | 11/2013 | Milbocker ......... A61N 1/36592 607/17 |

OTHER PUBLICATIONS

Ambrosi, C., et al., "Termination of sustained atrial flutter and fibrillation using low voltage multiple shock therapy", Heart Rhythm, Jan. 2011, vol. 8, No. 1, pp. 101-108.

* cited by examiner

FIG. 1A
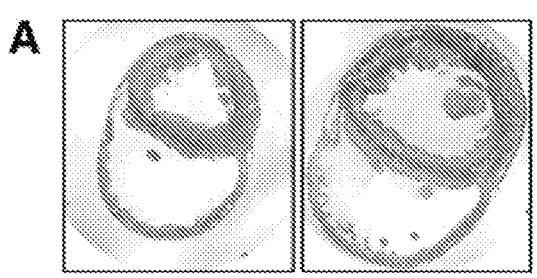
FIG. 1B
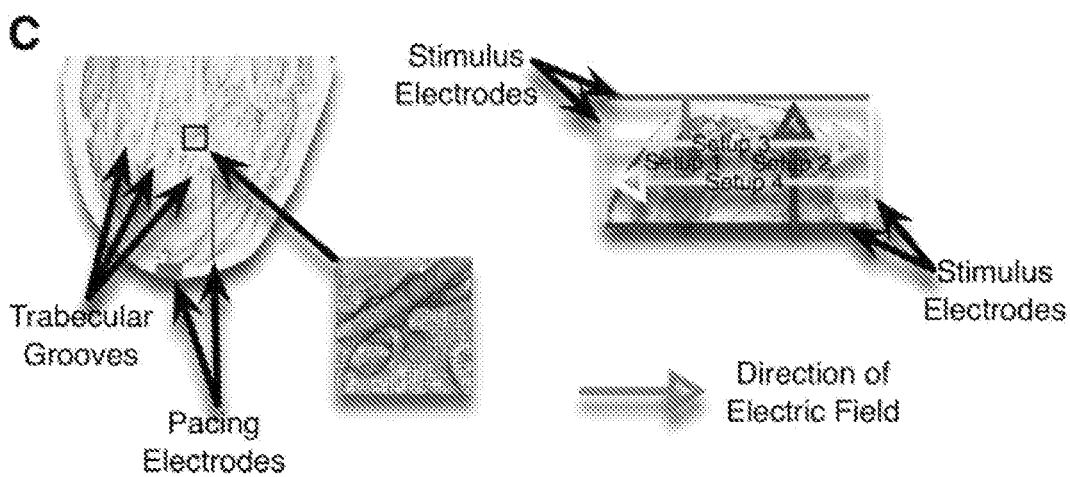
FIG. 1C

US 9,623,258 B2

METHOD FOR LOW VOLTAGE DEFIBRILLATION WITH FAR-FIELD STIMULI OF VARIABLE TIMINGS BASED ON FEEDBACK FROM THE HEART

CROSS-REFERENCE TO RELATED APPLICATIONS

This application is a 35 U.S.C. §371 U.S. national entry of International Application PCT/US2013/039680, having an international filing date of May 6, 2013, which claims the benefit of U.S. Provisional Application No. 61/642,822, filed May 4, 2012, the content of each of the aforementioned applications is herein incorporated by reference in their entirety.

GOVERNMENT SUPPORT

This invention was made with government support under R01 HL082729 awarded by the National Institutes of Health. The government has certain rights in the invention.

FIELD OF THE INVENTION

The present invention relates generally to cardiology. More particularly the present invention relates to a method for cardiac defibrillation, including low-voltage defibrillation.

BACKGROUND OF THE INVENTION

Defibrillation by strong electric shock remains the only known effective way of terminating ventricular fibrillation (VF) and, thus, preventing sudden cardiac death. However, strong shocks are associated with adverse effects including cellular injury from electroporation, cardiac conduction disturbances, mechanical dysfunction, increased mortality, and pain and psychological trauma. More than 100,000 implantable cardioverter-defibrillators (ICDs) are implanted annually in the United States alone. Regrettably, inappropriately delivered shocks remain common and over 13% of patients with an ICD receive one or more inappropriate shocks. The adverse effects of high-voltage shocks could be avoided or diminished if VF could be terminated reliably by defibrillation shocks of significantly lower voltage and energy. Hence, a method and device for low-voltage termination of VF would have important clinical applications.

Atrial fibrillation (AF), on the other hand, is the most common cardiac arrhythmia and can be chronic. AF can severely affect quality of life, and it can lead to severe complications such as stroke. The adverse effects of ventricular defibrillation hold true for atrial defibrillation as well, with two additional points to consider: 1) AF is not, per se, life-threatening, so the case for a potentially damaging therapy such as high-voltage defibrillation is not as strong as in VF, and 2) a strong defibrillation shock could induce potentially life-threatening ventricular arrhythmias. Hence, a method and device for low-voltage termination of AF would have potential clinical applications.

Recent experimental studies have shown that applied electric fields delivering multiple far-field stimuli can terminate ventricular tachycardia (VT), atrial flutter (AFl), and AF with less total energy than a single strong shock. Some of these studies used constant stimulation rates close to the arrhythmia cycle length (CL), whereas others used constant stimulation rates much faster than that CL. Since the mechanisms by which multiple far-field stimuli terminate arrhythmias are not well understood, it remains unknown which stimulation protocol (with constant or variable stimulation rates) would present the optimal benefit. Furthermore, it is unclear whether VF can also be terminated by multiple low-voltage, far-field stimuli.

It would therefore be advantageous to provide a method and device for low-voltage defibrillation of a patient.

SUMMARY

According to a first aspect of the present invention, a method for terminating fibrillation in a heart of a subject includes obtaining a cardiac signal and feedback from the heart of the subject and monitoring the cardiac signal for a fibrillation event. The method includes applying a first far-field stimulation to the heart of the subject. The first stimulation is configured to convert the fibrillation event into a tachycardia event, and a timing of said first far-field stimulation is determined using the feedback from the heart of the subject, or an estimate thereof. Additionally, the method includes applying a second stimulation to the heart of the subject, wherein said second stimulation is configured to terminate the tachycardia event.

In accordance with an aspect of the present invention, the method includes the cardiac signal being obtained using electrocardiography. The cardiac signal can be obtained using sensors positioned directly on the heart of the subject. The target time for applying stimulation to the heart of the subject can also be estimated. The target time is approximately the maximum amount of excitable tissue of the heart of the subject. The far-field stimulation is applied using at least one of a defibrillator, an internal cardioverter-defibrillator, or other implanted defibrillation device. It should be noted that the first far-field stimulation can take the form of a single far-field stimulus, or, alternately, can take the form of a series of far-field stimuli. Each stimulus in the series has a variable time of application determined using feedback or an estimate thereof from the heart of the subject. The first stimulation can take the form of multiple series of stimuli. Each multiple series of stimuli can have a variable time of application based on the feedback or an estimate thereof from the heart of the subject. Each stimulus in the multiple series can also have a variable time of application based on the feedback or an estimate thereof from the heart of the subject. The first far-field stimulation takes the form of one of either a monophasic or a biphasic shock, or an alternate shock waveform. The fibrillation event can take the form of a ventricular fibrillation event or an atrial fibrillation event. Similarly, the tachycardia event takes the form of a ventricular tachycardia event or an atrial flutter event.

In accordance with another aspect of the present invention, a device for providing low-voltage defibrillation of a heart of a subject includes a sensor configured for obtaining a cardiac signal and feedback from the heart of the subject and a source of electrical current configured for delivering stimuli to the heart of the subject. The device also includes a computer control loaded with a computer readable medium programmed to monitor the cardiac signal for a fibrillation event. The computer is also programmed to apply a first far-field stimulation to the heart of the subject. The first stimulation is configured to convert the fibrillation event into a tachycardia event. A timing of said first far-field stimulation is delivered using the feedback from the heart of the subject. A second stimulation is applied to the heart of the subject. The second stimulation is configured to terminate the tachycardia event.

In accordance with another aspect of the present invention, the source of electrical current takes the form of external defibrillator pads in electrical communication with the source of electrical current. Alternately, the source of electrical current takes the form of internal stimulators positioned directly on the heart of the subject, or the form of internal stimulators positioned without direct contact to the heart of the subject. Further, the source of electrical current includes a battery. The computer control can take the form of one of a microprocessor, computer processor, or computing device. The computer readable medium is further programmed to approximate a time for delivery of stimulus. The time for delivery of stimulus is based on an estimate of stimulus, if no data on the timing can be obtained. The sensors, source of electrical current, and stimulators can all be in wired or wireless communication with the computer control. The computer control can be configured to transmit information to a number of different computing devices for patient monitoring, update of the device, or any other suitable purpose known to or conceivable by one of skill in the art. The sensors, source of electrical current, and stimulators are in electrical communication with one another.

In accordance with still another aspect of the present invention, a method for terminating fibrillation in a heart of a subject includes obtaining a cardiac signal and feedback from the heart of the subject. The method also includes monitoring the cardiac signal for a fibrillation event. Additionally, the method includes applying a train of far-field stimuli (≥1) to the heart of the subject when the timing of each stimulus in the train of far-field stimuli is determined using the feedback from the heart of the subject.

In accordance with yet another aspect of the present invention, the train of far-field stimuli of the heart of the subject can be configured to convert the fibrillation event into a tachycardia event. The method further includes terminating the tachycardia event. Alternately, the train of far-field stimuli of the heart of the subject can be configured to terminate the fibrillation event directly. The timing of each of the stimuli in the train of stimuli can be estimated. It should be noted that the tachycardia event can take the form of an atrial flutter event. A single far-field stimulus, a train of far-field stimuli, or multiple trains of stimuli can be used as the first stimulation. The timing of the stimuli can be based on feedback from the heart to coincide with maximal or large amounts of excitable tissue, or an estimate thereof.

In accordance with still another method of the present invention, a method for terminating fibrillation in a heart of a subject includes obtaining a cardiac signal from the heart of the subject. The method also includes monitoring the cardiac signal for a fibrillation event. Additionally, the method includes applying a far-field stimulation to the heart of the subject, wherein the far-field stimulation is configured to convert the fibrillation event into a tachycardia event.

BRIEF DESCRIPTION OF THE DRAWINGS

The accompanying drawings provide visual representations which will be used to more fully describe the representative embodiments disclosed herein and can be used by those skilled in the art to better understand them and their inherent advantages. In these drawings, like reference numerals identify corresponding elements and:

FIG. 1A illustrates sample magnetic resonance imaging (MRI) slices taken from apical and basal positions.

FIG. 1B illustrates the sample MRI slices of FIG. 1A after bath removal, segmentation, and cropping of right ventricular (RV) wall.

FIG. 1C illustrates long and short axis views of the high resolution rabbit RV model.

DETAILED DESCRIPTION OF THE PREFERRED EMBODIMENTS

Figure 2A:
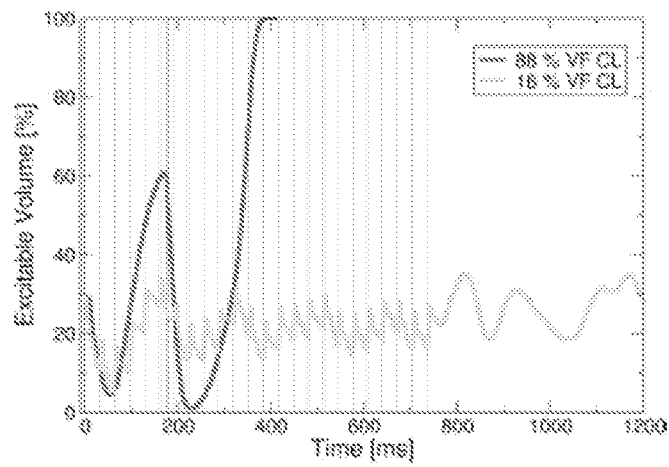
FIG. 2A illustrates the volume of excitable tissue (measured as percentage of excitable nodes in the mesh) during successful defibrillation at 88% VF CL (red) and failed defibrillation at 16% VF CL (green) after 500 mV/cm stimuli.

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention includes a method for providing defibrillation to a subject, specifically, but not exclusively, low-voltage defibrillation. The method includes converting ventricular fibrillation (VF) of the subject's heart into ventricular tachycardia (VT), but this method can also be applied to converting atrial fibrillation (AF) of the subject's heart into atrial flutter (AFl). Therefore, throughout the application, cardiac fibrillation will be used to refer to both VF and AF and cardiac tachycardia will be used in order to refer to both VT and AFl. Tachycardia is then terminated in a second stage, as is described below. The method can also be applied to terminate fibrillation directly, without converting to tachycardia first. The termination of fibrillation (altogether or by conversion to tachycardia) is achieved using feedback from the heart to time the far-field defibrillation stimuli, or if feedback data is not available, an estimate thereof. Stimuli are timed to coincide closely with the maximum amount of excitable tissue. The resultant tachycardia can then be terminated using a tachycardia termination protocol. The tachycardia termination protocol can take the form of an established tachycardia termination protocol or any other protocol known to or conceivable by one of skill in the art.

The method can be implemented using a currently available defibrillator or a currently available internal cardioverter-defibrillator (ICD) configured to apply a far-field stimulus. Alternately, a device designed especially for the method can also be used. Because the proposed defibrillation method requires less energy than the current standard approach of one single biphasic stimulus, ICD battery life could be improved or the battery made smaller. The method also reduces pain to patients and reduce cellular and tissue damage resultant from a single biphasic shock. The method also has the potential of terminating cardiac fibrillation earlier than other methods of low-voltage defibrillation using predetermined, non-variable stimulation rates, which is especially significant from a hemodynamic standpoint.

More particularly, with respect to the present method, a signal is obtained from a heart of a subject and is monitored to determine cardiac rhythm, and in particular cardiac fibrillation. If cardiac fibrillation is detected and defibrillation becomes necessary, the signal from the heart is used to determine appropriate timing for treatment. The signal can be obtained in a number of different ways known to or conceivable by one of skill in the art. For instance, the signal can be obtained by implanting sensing electrodes in the heart or using electrocardiography (ECG) recordings. However, these examples are not meant to be considered limiting, and any suitable means of obtaining a cardiac signal could be used. The signal from implanted sensing electrodes can then be processed and monitored to determine when to apply electric stimuli. Similarly, if ECG is used, the output from these recording can be correlated to the amount of excitable tissue in order to determine when to apply electric stimuli.

The timing of when to apply the far-field electrical stimuli is determined through the processing of the signal from the heart, or alternately, if signal is not available the timing of when to apply the electrical stimuli can also be estimated. The signal obtained from the heart includes information regarding the amount of excitable tissue present in the heart. Therefore, defibrillation stimuli, or in particular, low-voltage defibrillation stimuli, are applied to the heart of the subject when a large amount of excitable tissue is present in the heart of the subject. If an estimate is going to be used, stimuli can be delivered when the amount of excitable tissue is estimated to be large. Alternately, any other suitable approximation known to or conceivable by one of skill in the art could also be used. If a train of stimuli is used, it should be noted that each of the stimuli in the train can have variable timing based on the feedback from the heart. Similarly, if multiple trains of stimuli are used, the timing of each train can be variable based on the feedback from the heart and in turn each stimulus in the train can also have variable timing based on the feedback from the heart.

Alternately, if signal from the heart of the subject is not available, a device for implementing the defibrillation can be programmed to estimate the best timing of defibrillation. For example, the device for implementing the defibrillation could be programmed to estimate the amount of excitable tissue based on cardiac fibrillation cycle length (1/dominant frequency). Other estimations could be used as well. Stimuli would be delivered while enough tissue is excitable to convert cardiac fibrillation to cardiac tachycardia.

In accordance with the present method, after cardiac fibrillation is detected and timing for the stimulus is determined, a first stimulation is delivered to the heart of the subject at the determined time. It should be noted that while the term first stimulation is used, the stimulation can take the form of one far-field stimulus, a single series of far-field stimuli, or multiple series of stimuli. The number of stimuli or the number of the series of stimuli can be determined based on the feedback from the signal of heart. The first stimulation can take the form of monophasic or biphasic stimuli, and can be delivered by a traditional defibrillator, ICD, device created especially for the implementation of the method of the present invention, or another suitable device known to or conceivable by one of skill in the art. Alternately, the first stimulation can take the form of any other suitable waveform known to or conceivable by one of skill in the art. The first stimulation is delivered to convert the cardiac fibrillation to cardiac tachycardia. Converting cardiac fibrillation to cardiac tachycardia requires less voltage than the traditional single biphasic shock used to terminate cardiac fibrillation. After cardiac fibrillation is converted to cardiac tachycardia, a second stimulation is administered in order to terminate the cardiac tachycardia. Similarly to the first stimulation, the second stimulation can take the form of a single stimulus, multiple stimuli, a series of stimuli, or multiple series of stimuli. Also, the cardiac tachycardia can be terminated using electroshock, pacing, or any other suitable means known to or conceivable by one of skill in the art. For instance, cardiac tachycardia can be terminated with a series of far-field stimulation delivered using a traditional defibrillator, ICD, device created especially for the implementation of the method of the present invention, or another suitable device known to or conceivable by one of skill in the art.

A device configured to execute the method of the present invention can also be provided. The device can include sensors for obtaining a cardiac signal from the heart of the subject. The device can also include a source of electrical current for delivering stimuli to the heart of the subject. The source of electrical current can be transmitted to the heart through external defibrillator pads in electrical communication with the source of electrical current. Alternately, the source of electrical current can be coupled to internal stimulators positioned directly on the heart of the subject, or internal stimulators positioned away from the heart, but including the heart in the delivered electric field. Given the reduced voltage required by the method of the present invention, a lower voltage/smaller battery can be used as the source or electrical current. Additionally, the device can include a computer control such as a microprocessor, other computer processor, or computing device loaded with a computer readable medium programmed to implement the method of the present invention. The computer readable medium can be programmed to monitor the cardiac signal for fibrillation. When fibrillation is detected, the computer readable medium can also be programmed to determine when a stimulus should be delivered to the heart of the subject. If signal is not available, the computer readable medium can also be programmed to approximate a time for delivery of stimulus, as described above. The sensors, source of electrical current, and stimulators can all be in wired or wireless communication with the computer control. Further, the computer control can be configured to transmit information to a number of different computing devices for patient monitoring, update of the device, or any other suitable purpose known to or conceivable by one of skill in the art. The sensors, source of electrical current, and stimulators can also be in electrical communication with one another.

EXAMPLE

An exemplary implementation of the present invention is described herein, in order to further illustrate the present invention. The exemplary implementation is included merely as an example and is not meant to be considered limiting. Any implementation of the present invention on any suitable subject known to or conceivable by one of skill in the art could also be used, and is considered within the scope of this application.

A brief overview of the methods is presented in this and the next paragraph, and detailed information is provided in the subsequent paragraphs. In short, a computational bidomain model of a rabbit right ventricle (RV) was developed, featuring cardiac microstructure such as trabeculations and major coronary vessels, as illustrated in FIGS. 1A and 1B. Four different electric field directions were used in the simulations. These "setups" are illustrated in FIG. 1C.

Sustained VF was induced in the model and low-voltage stimuli (all strengths were ≤1 V/cm) were delivered to terminate the arrhythmia. To terminate VF, multiple (up to 12) far-field stimuli of various strengths were applied at different stimulation rates. No stimuli were applied in the control case. Tissue was considered excitable when transmembrane potential ($V_m$) was ≤−70 mV.

More particularly, with respect to the example, a very high resolution structurally-detailed finite element model of a rabbit RV was developed. High-resolution ex-vivo magnetic resonance imaging (MRI) scans of the rabbit ventricles were acquired at a voxel resolution of 26.4×26.4×24.4 µm³, as illustrated in FIG. 1A. Following segmentation, the images were cropped to include only the RV free wall, as shown in FIG. 1B. A highly detailed finite element mesh was then developed. The mesh of the RV and the surrounding bath consisted of 29 million elements and 5 million nodes and had overall dimensions of 8×17×14 mm. The RV mesh had a mean edge length of 59 µm.

At this resolution, the mesh was fine enough to accurately represent endocardial microstructures such as trabeculae carnae and trabecular grooves, as well as the major vessels of the coronary vasculature, as illustrated in FIG. 1C. Fiber orientation, which could not be acquired at that resolution with MRI, was assigned to the model using a novel rule-based algorithm, the performance of which had been thoroughly validated. The model RV was submerged in a perfusing bath. Representing one of the most complex bidomain models to date, the computational mesh of the resulting finite element model had 15 million elements, 3 million nodes, and a mean edge length of 59 µm in the tissue, and an additional 13 million elements and 2 million nodes in the bath. The model was subjected to multiple low-voltage stimuli. In this study, low-voltage stimuli is defined as far-field stimuli of 1 V/cm or lower voltage. Previously, stimulus strengths as high as 3.6 V/cm have been considered low-voltage, and stimuli around or over 5 V/cm are generally considered "standard" voltage. The electric stimuli were delivered through plate electrodes located at the boundaries of the perfusing bath. Four different electric field directions were used in the simulations, as illustrated in FIG. 1C.

Ionic properties were modeled with the Mahajan-Shiferaw model of the rabbit ventricular myocyte. The mathematical description of current flow in cardiac tissue was based on the bidomain representation. The bidomain equations were solved with the Cardiac Arrhythmia Research Package (CARP). The numerical techniques used in CARP have been described extensively elsewhere.

The choice of the model was dictated by the hypothesis that the detailed microanatomy of the heart is an essential player in the ability of multiple low-voltage stimuli to alter the electrical behavior of the heart. To represent the microstructure but also keep the model computationally tractable (in a bidomain representation), a model of a portion of the heart (the RV) was used, and not the entire organ. To represent all possible scenarios where a ventricular wall could be subjected to different directions of the applied fields, four different field orientations were used. Reentry was initiated with S1-S2 "pinwheel" stimulation after apical pacing (see left panel of FIG. 1C for electrode locations).

Different electrode setups were used in order to represent various scenarios where the ventricular wall was subjected to electric fields of different directions; however, it was not an objective of this study to evaluate one electrode setup's performance against another. It was, however, the objective to evaluate various stimulation rates' abilities to cardiovert. Hence, means were taken over the electrode setups to be able to compare stimulation rates' defibrillation success rates, as illustrated in FIG. 5.

Initially, sustained ventricular fibrillation (VF) was not induced in the model due to the small size of the rabbit RV. Therefore, the dimensions of the model were increased by a factor of five for the VF studies in order to provide enough tissue for VF wavefronts to propagate. In order to get a steeper restitution curve and to promote wavebreak and, thereby, promote VF formation and maintenance, the R(V) parameter of the $I_{Ca,L}$ recovery kinetics in the Mahajan-Shiferaw model were increased by a factor of 1.5. VF was induced by rapid pacing from the apex. Far-field stimuli were applied from the two electrode configurations (setups 1 and 2; see FIG. 1C), except for a few select simulations where all four electrode configurations were used.

The VF CL was defined as the inverse of the mean dominant frequency (DF). The DF over 2 s of VF was computed for every node in the RV mesh by constructing a Fast Fourier Transformation in time and then determining the frequency that corresponded to the largest magnitude. The VF CL was found to be 201 ms. In line with protocols used in experimental studies, up to 12 10 ms far-field stimuli were given at 88% of VF CL, and up to 24 in number 5 ms stimuli were given at 16% of VF CL. We chose a shorter stimulus length for the fastest stimulation rate (16% VF CL) to provide the tissue with enough time to recover between stimuli. The maximum number of stimuli at 16% VF CL was doubled compared to the other stimulation rates, from 12 to 24, because every individual stimulus was only half as long as that for the other rates (5 vs. 10 ms). The waveform of the stimuli was monophasic rectangular, but biphasic stimuli could have been used as well. Diastolic activation thresholds for monophasic stimuli were 55 mV/cm for setup 1 and 70 mV/cm for setup 2. Stimuli above (250, 500 mV/cm) the diastolic activation threshold were delivered. In comparison, the defibrillation shocks used today clinically generally create a voltage gradient of at least 5 V/cm. The defibrillation threshold (DFT) is defined as the lowest energy high-voltage shock or low-voltage stimulation protocol to successfully terminate VF. The arrhythmia was considered to be successfully terminated if no propagation was present 0.5 s after the last stimulus. No defibrillation stimuli were applied in the control case. VF in the control case continued for as long as simulated (>2 s after the first stimulus was applied in defibrillation simulations).

The tissue was defined as excitable when it had $V_m$ values≤−70 mV, and as excited when $V_m$ was ≥−10 mV. The volume of excitable tissue was measured as percentage of excitable nodes in the mesh, whereas the volume of excited tissue was measured as percentage of excited nodes. The terms volume of excitable volume, excitable gap, and excitable volume are used interchangeably. In addition to stimuli given at a set rate, stimuli were also applied at timings of maximum excitable or excited volume.

Virtual electrode polarizations (VEPs; depolarizing and hyperpolarizing changes in $V_m$ in response to an applied electric field) were strongest at the trabecular grooves, and at the tip of the preexisting wavefront. Consistent with the preliminary results, earliest endocardial activations after a field stimulus occurred at the trabecular grooves. These observations underscore the significance of the endocardial structures—in particular, the trabecular grooves—in the tissue response to low-voltage far-field stimuli. Even when VEPs did not elicit new activations (sub-threshold stimuli), the propagation of the reentrant wave was altered.

FIG. 2A shows the time course of the volume of excitable tissue in the model preparation during two defibrillation attempts (88% & 16% VF CL). Defibrillation was successful after only two stimuli in the 88% case, but was unsuccessful in the 16% case. In both cases, the cumulative effects of positive and negative VEPs caused a decrease in the amount of excitable tissue immediately after a stimulus, as tissue was depolarized by positive VEPs, and as propagation quickly captured tissue made excitable by negative VEPs. In the 88% case, excitable volume subsequently increased, as tissue repolarized, and the next stimulus of the train was able to capture a large amount of excitable tissue. However, when the stimulation rate was 16% of VF CL, the tissue did not have time to recover from the previous stimulus, and no significant increase in excitable volume took place before the next stimulus. Thus, the faster stimuli (16% VF CL) were not able to capture large amounts of tissue and thus eliminate the excitable gap for propagation, which ultimately led to a reduced defibrillation success rate in this case as compared to that for the slower stimulation rate (88% VF CL).

Figure 2B:
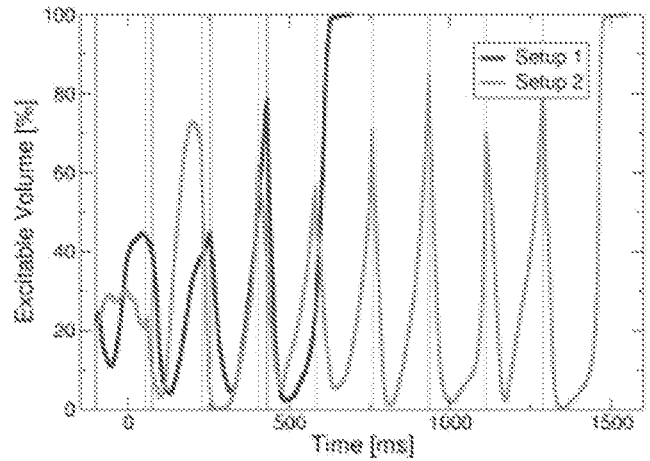
FIG. 2B illustrates the excitable volume during successful 500 mV/cm, 88% VF CL defibrillation stimuli delivered at different "phases" of VF.

Analyzing the excitable volume for 88% VF CL low-voltage defibrillation episodes at different VF "phases" (different timings of the first stimulus), it was observed that stimuli delivered when the excitable volume was particularly large were especially successful, as illustrated in FIG. 2B, irrespective of the electrode setup.

Figure 3A:
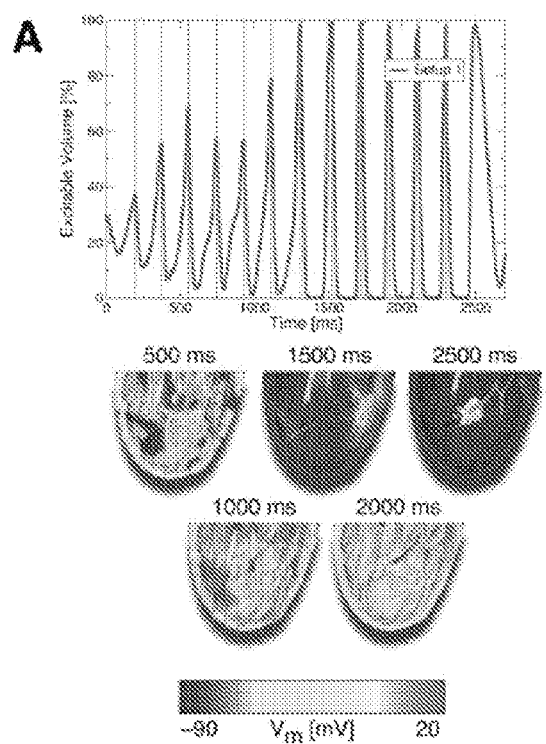
FIG. 3A illustrates the excitable volume during a defibrillation attempt from electrode setup 1 where 250 mV/cm stimuli were delivered at timings when the amount of excitable tissue was maximal, and transmembrane potential ($V_m$) maps of defibrillation attempts.
Figure 3B:
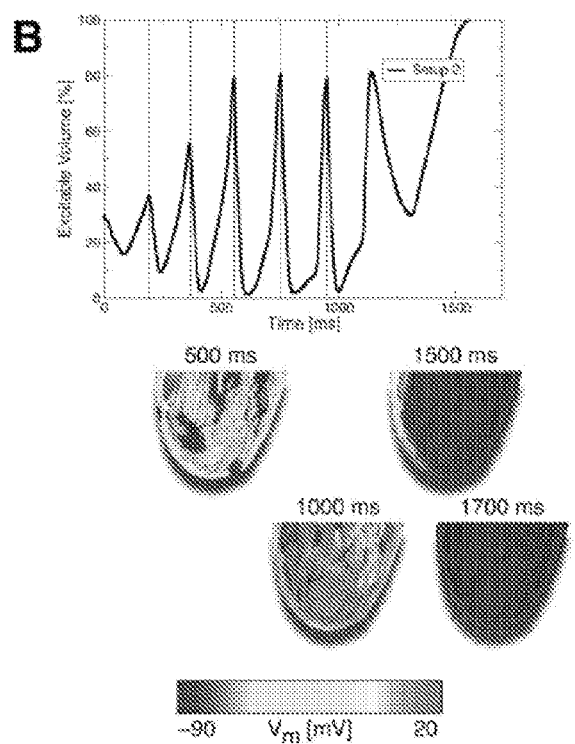
FIG. 3B illustrates excitable volume during defibrillation attempt, where 250 mV/cm stimuli were delivered at timings when the excitable tissue was maximal, and $V_m$ maps of defibrillation attempts. VF was converted to VT, and VT was then terminated with additional stimuli from setup 2. Thin vertical lines in top panels mark onsets of stimuli.

Based on this observation, it was then attempted to defibrillate by applying low-voltage far-field stimuli at the times when tissue excitable volume was maximum (the excitable gap was largest), as opposed to applying stimuli at a set rate. Stimuli of the lowest supra-threshold strength were chosen from the defibrillation protocol for this set of simulations, 250 mV/cm. FIG. 3A shows the excitable volume in the preparation and sample $V_m$ maps at specific timings for stimuli applied from electrode setup 1; corresponding plots for setup 2 are presented in FIG. 3B. Stimuli applied at excitable volume maxima converted VF into VT ($V_m$ maps in FIGS. 3A and 3B) in both cases. The VT was subsequently terminated by the continuing stimuli for setup 2 (FIG. 3B), while stimuli from setup 1 failed to do so (FIG. 3A; case addressed below). In both cases, conversion from VF into VT was achieved because the appropriately timed low-voltage stimuli "synchronized" tissue depolarization. Stimuli applied when the excitable gap was large were able to capture large amounts of tissue. This is evidenced by the fact that the amount of excitable tissue at stimulus-onset was consistently above 75%, and the post-stimulus minimum amount of excitable tissue was below 5% from the third stimulus onwards (setup 2, FIG. 3B) or from the sixth stimulus onwards (setup 1, FIG. 3A), respectively. The captured tissue then depolarized and repolarized at approximately the same time. This mechanism converted VF into VT after only a few low-voltage stimuli.

Figure 4A:
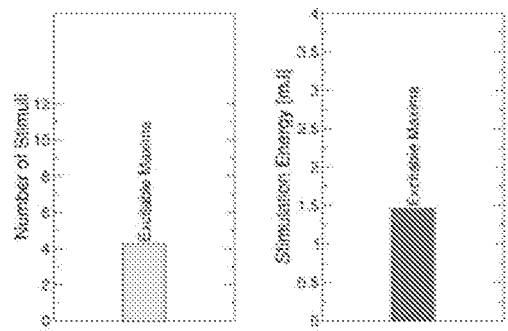
FIG. 4A illustrates a mean number of stimuli and energy required for successful conversion of VF into VT when stimulated at a strength of 250 mV/cm when excitable volume was maximal, averaged over all four electrode setups.
Figure 4B:
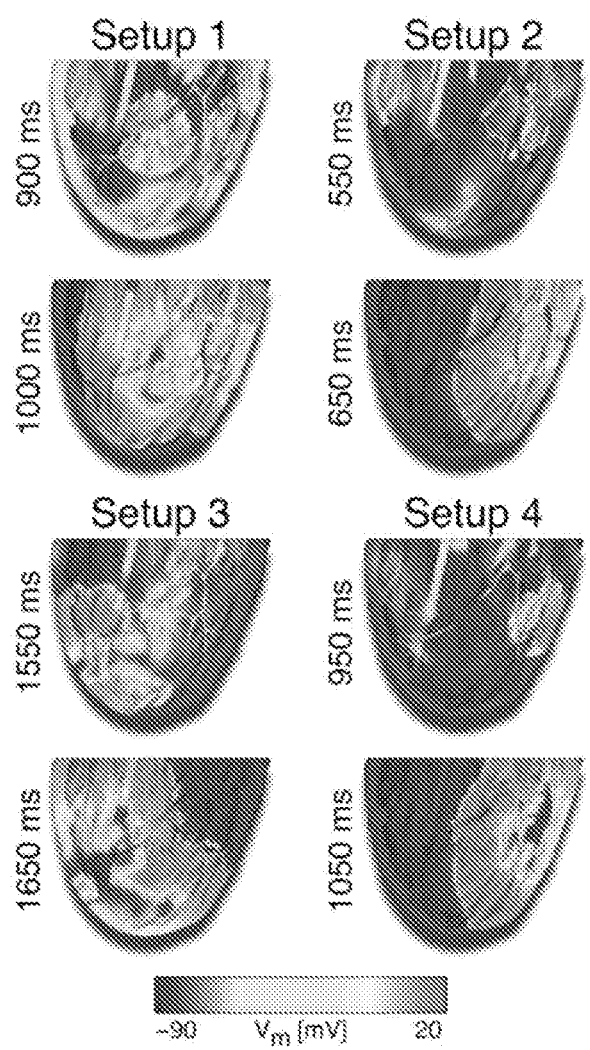
FIG. 4B illustrates $V_m$ maps of simulations showing the resulting VT for all four electrode setups.

FIGS. 4A and B show that stimuli applied when excitable volume was maximal successfully converted VF into VT for all four electrode setups (i.e., including the less favorable setups 3 and 4) with, on average, 4.25 stimuli of 250 mV/cm strength, with an average total energy of 1.47 mJ, demonstrating that conversion of VF to VT by stimulating when the excitable gap was largest was independent of the applied field direction.

Figure 5A:
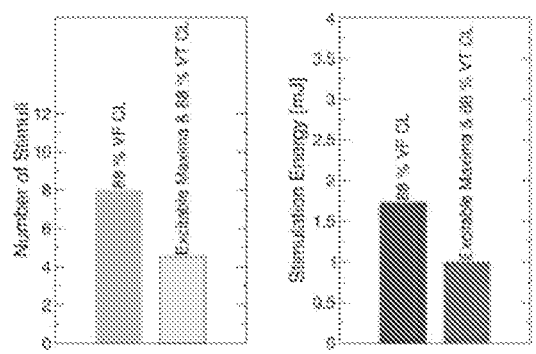
FIG. 5A illustrates a comparison of the mean number of stimuli and energy required for successful defibrillation following 250 mV/cm stimuli at 88% VF CL and using the two-stage defibrillation protocol (means taken over electrode setups).
Figure 5B:
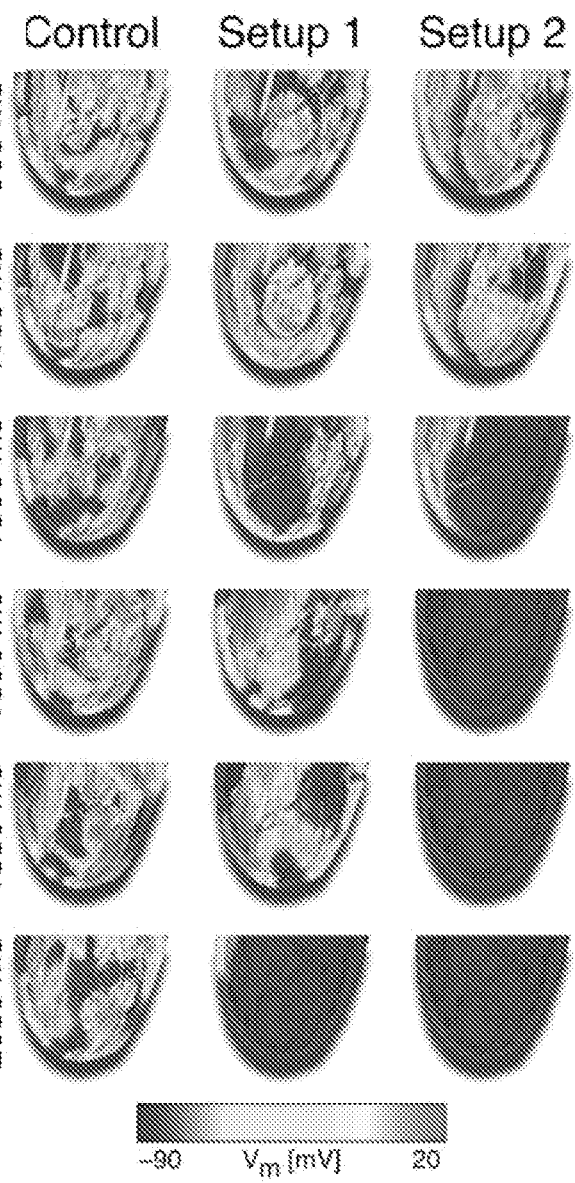
FIG. 5B illustrates $V_m$ maps of successful defibrillation with the two-stage defibrillation protocol compared to control $V_m$ maps. With this two-stage defibrillation protocol, VF was converted into VT, which was then successfully terminated.

While the above protocol always converted VF into VT, it did not always terminate VT (FIG. 3A). Termination of VT failed in that case because each stimulus was delivered at the same instant of the VT cycle each time, when it did not perturb the stable rotor. Therefore, a two-stage defibrillation protocol was applied: First, VF was converted into VT with the application of multiple low-voltage stimuli at times when the amount of excitable tissue was maximal. Second, low-voltage stimuli at 88% of VT CL were applied to terminate VT. With the addition of this second stage, VT could now be terminated (compare lower panels of FIG. 3A with middle panel of FIG. 5B). The number of stimuli and the energy required for successful defibrillation with this two-stage defibrillation protocol as compared to the case when stimuli were applied at 88% VF CL are presented in FIG. 5A, while FIG. 5B shows $V_m$ maps of the two-stage defibrillation protocol compared to control (no applied stimuli) at different times.

The number of stimuli required for successful two-stage defibrillation at 250 mV/cm was 56.25% of the number of stimuli required at 88% VF CL stimulation rate (4.5 vs. 8), and the total energy for successful two-stage defibrillation was 57.42% of the energy required at 88% VF CL rate (0.99 vs. 1.73 mJ; FIG. 5A).

Figure 6A:
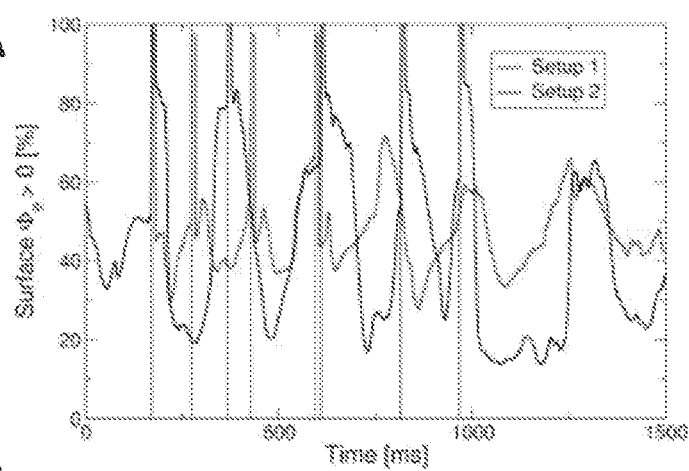
FIG. 6A illustrates a surrogate measure for the excitable volume (percentages of surface nodes with extracellular potential, $\Phi_e > 0$ mV) during delivery of the first stage of the proposed two-stage low-voltage defibrillation protocol.
Figure 6B:
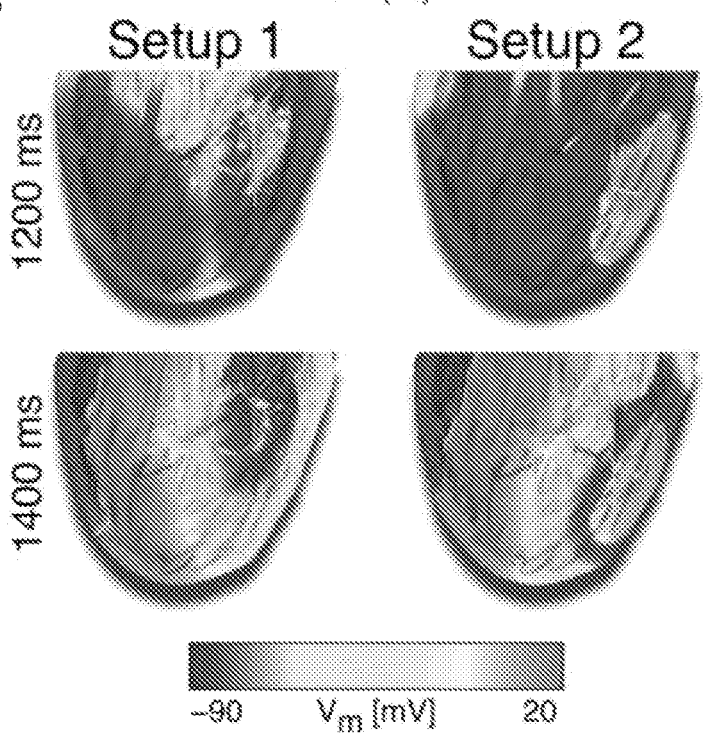
FIG. 6B illustrates $V_m$ maps of the defibrillation events corresponding to FIG. 6A.

While the excitable gap cannot currently be directly assessed experimentally or clinically, extracellular potential ($\Phi_e$) can be measured. Since $V_m = \Phi_i - \Phi_e$, where $\Phi_i$ is the intracellular potential, $V_m$ and $\Phi_e$ are related. Myocardial cell activation is driven by an inward transmembrane current flux. Thus, $\Phi_e$ is negative during peak action potential, when the cell is activated. On the other hand, negative $V_m$ (tissue was considered excitable if $V_m \leq -70$ mV) is generally associated with positive $\Phi_e$. While there is no known threshold value $\chi$ for which $\Phi_e > \chi$ mV would correspond exactly to $V_m \leq -70$ mV, it was hypothesized that positive $\Phi_e$ values can provide an estimate for tissue excitability. As a proof of principle, the extent of the myocardial surface was used with $\Phi_e > 0$ mV as a surrogate of the volume of the excitable tissue. In order to convert VF into VT in the first stage of a two-stage defibrillation protocol, instead of stimulating when the excitable volume was maximal, stimuli were now timed to coincide with the maximum number of surface nodes experiencing positive $\Phi_e$ values (as long as that maximum occurred at a timing of at least 50% of VF CL after the previous stimulus). Using this surrogate measure of the extent of the excitable gap, VF was successfully converted into VT (FIGS. 6A and 6B). VF was converted into VT with four 250 mV/cm stimuli from electrode setup 1, or with five 250 mV/cm stimuli from electrode setup 2.

The exemplary implementation of the present method described herein illustrates, at the least, that:

1. Multiple low-voltage far-field stimuli can terminate VT and VF in the model,

2. Far-field stimuli administered at timings when the excitable volume is maximal (i.e., using electrical data gathered from the myocardium as feedback to appropriately time each stimulus) successfully convert VF into VT, and 3. Termination of VF using a novel two-stage defibrillation protocol is achieved with fewer stimuli and less total energy than with protocols using a set stimulation rate (16% or 88% of VF CL).

The two-stage defibrillation protocol of the present invention uses the amount of the excitable volume to time stimulus delivery, but the excitable volume cannot be measured directly. Surface $\Phi_e$, on the other hand, could be measured using electrodes. As a proof of concept, it was shown that the first stage of the protocol also works if the extent of tissue with $\Phi_e > 0$ mV on the myocardial surface is used as a rough surrogate measure of the volume of excitable tissue. This provides an avenue for future research and device development to bring this two-stage defibrillation protocol to the clinic.

The exact human pain threshold for defibrillation shocks is not known, but it has been shown that the threshold lies at or below 400 mJ. The average total energy required for successful defibrillation with the proposed two-stage defibrillation method at 250 mV/cm was 0.99 mJ, but low-voltage defibrillation in humans will require more energy than that. Nevertheless, low-voltage defibrillation below the pain threshold can be achieved with this novel two-stage protocol.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims. It should be noted that while the present invention is described with respect to terminating ventricular fibrillation it could also be applied to atrial fibrillation in a similar manner.

The invention claimed is:

1. A method for terminating fibrillation in a heart of a subject comprising:
   obtaining a cardiac signal from the heart of the subject;
   monitoring the cardiac signal for a fibrillation event;
   applying a first far-field, low-voltage stimulation to the heart of the subject, wherein said first far-field stimulation is configured to convert the fibrillation event into a tachycardia event and a target time of said first far-field stimulation is determined using the signal from the heart of the subject, or an estimate thereof; and
   applying a second far-field, low-voltage stimulation to the heart of the subject, wherein said second stimulation is configured to terminate the tachycardia event.

2. The method of claim 1 further comprising the cardiac signal being obtained using electrocardiography.

3. The method of claim 1 further comprising the cardiac signal being obtained using sensors positioned directly on the heart of the subject.

4. The method of claim 1 further comprising estimating the target time for applying the first far-field, low-voltage stimulation to the heart of the subject.

5. The method of claim 1 further comprising the target time being at approximately a time correlated to the the maximum amount of excitable tissue of the heart of the subject.

6. The method of claim 1 wherein the first and second far-field, low-voltage stimulation are applied using at least one of a defibrillator, an internal cardioverter-defibrillator, or other implanted defibrillation device.

7. The method of claim 1 wherein the first far-field stimulation takes the form of a single far-field stimulus.

8. The method of claim 1 wherein the first far-field stimulation takes the form of a series of far-field stimuli.

9. The method of claim 8 wherein each stimulus in the series has a variable time of application determined using the signal or an estimate thereof from the heart of the subject.

10. The method of claim 1 wherein the first far-field, low voltage stimulation takes the form of multiple series of stimuli.

11. The method of claim 10 wherein each multiple series of stimuli have a variable time of application based on the signal or an estimation thereof from the heart of the subject.

12. The method of claim 11 wherein each stimulus in the multiple series has a variable time of application based on the signal or an estimation thereof from the heart of the subject.

13. The method of claim 1 wherein the first far-field, low-voltage stimulation takes the form of one of either a monophasic or a biphasic shock, or an alternate shock waveform.

14. The method of claim 1 wherein the fibrillation event takes the form of a ventricular fibrillation event.

15. The method of claim 1 wherein the tachycardia event takes the form of a ventricular tachycardia event.

16. The method of claim 1 wherein the fibrillation event takes the form of an atrial fibrillation event.

17. The method of claim 1 wherein the tachycardia event takes the form of an atrial flutter event.

18. A system for providing low-voltage defibrillation of a heart of a subject comprising:
   a sensor configured for obtaining a cardiac signal from the heart of the subject;
   a source of electrical current configured for delivering stimuli to the heart of the subject;
   a computer control loaded with a non-transitory computer readable medium programed to:
   monitor the cardiac signal for a fibrillation event;
   apply a first far-field, low-voltage stimulation to the heart of the subject, wherein said first far-field, low-voltage stimulation is configured to convert the fibrillation event into a tachycardia event and a timing of said first far-field, low-voltage stimulation is delivered using the signal from the heart of the subject; and
   apply a second far-field, low-voltage stimulation to the heart of the subject, wherein said second far-field, low-voltage stimulation is configured to terminate the tachycardia event.

19. The system of claim 18 wherein the source of electrical current takes the form of external defibrillator pads in electrical communication with the source of electrical current.

20. The system of claim 18 wherein the source of electrical current takes the form of internal stimulators positioned directly on the heart of the subject, or the form of internal stimulators positioned without direct contact to the heart of the subject.

21. The system of claim 18 wherein the source of electrical current comprises a battery.

22. The system of claim 18 wherein the non-transitory computer control comprises one of a microprocessor, computer processor, or computing device.

23. The system of claim 18 wherein the computer readable medium is further programmed to approximate a time for delivery of stimulus.

24. The system of claim 23 wherein the time for delivery of stimulus is based on an estimation of stimulus if no data on the timing can be obtained.

25. The system of claim 18 wherein the sensors, source of electrical current, and stimulators are all in wired or wireless communication with the computer control.

26. The system of claim 18 wherein the computer control is configured to transmit information to a number of different computing devices for patient monitoring, update of the device, or any other suitable purpose known to or conceivable by one of skill in the art.

27. The system of claim 18 wherein the sensors, source of electrical current, and stimulators are in electrical communication with one another.

* * * * *